(12) United States Patent
Keil et al.

(10) Patent No.: US 7,541,464 B2
(45) Date of Patent: Jun. 2, 2009

(54) 7-AZAINDOLES, PHARMACEUTICAL COMPOSITIONS AND THEIR THERAPEUTIC APPLICATIONS

(75) Inventors: Stefanie Keil, Hofheim (DE); Maike Glien, Wiesbaden (DE); Hans-Ludwig Schaefer, Hochheim (DE); Wolfgang Wendler, Selters (DE); Patrick Bernardelli, Villepreux (FR); Corinne Terrier, Livry Gargan (FR); Baptiste Ronan, Clamart (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/681,923

(22) Filed: Mar. 5, 2007

(65) Prior Publication Data

US 2007/0254908 A1     Nov. 1, 2007

Related U.S. Application Data

(63) Continuation of application No. PCT/EP2005/009269, filed on Aug. 27, 2005.

(30) Foreign Application Priority Data

Nov. 9, 2004    (EP)   .................................. 04021667

(51) Int. Cl.
| | |
|---|---|
| C07D 471/00 | (2006.01) |
| C07D 471/02 | (2006.01) |
| A61K 31/01 | (2006.01) |
| A61K 31/03 | (2006.01) |
| A01N 47/00 | (2006.01) |
| A61K 31/015 | (2006.01) |
| A61K 31/02 | (2006.01) |
| A61K 31/025 | (2006.01) |

(52) U.S. Cl. ........................................ 546/113; 514/300
(58) Field of Classification Search .................. 546/113
See application file for complete search history.

(56) References Cited

FOREIGN PATENT DOCUMENTS

EP           1445258      8/2004
WO    WO 2004/074284    9/2004
WO    WO 2004074284 A1 *   9/2004

\* cited by examiner

*Primary Examiner*—Johann R Richter
*Assistant Examiner*—Courtney Brown
(74) *Attorney, Agent, or Firm*—Jiang Lin

(57) ABSTRACT

The present invention relates generally to compounds and compositions for the treatment of metabolic diseases and specifically, the present invention relates to compounds that therapeutically modulation and control lipid and/or carbohydrate metabolism and are thus suitable for the prevention and/or treatment of diseases such as type 2 diabetes, atherosclerosis, and the diverse manifestations thereof. The present invention relates to 7-azaindoles, their physiologically acceptable salts and functional derivatives thereof that exhibit a high degree of peroxisome proliferator-activated receptors (PPAR) agonist activity. Compounds of the present invention are described by formula I:

Formula 1 in which the R-groups are herein defined, together with their pharmaceutically acceptable salts, therapeutic methods for their use and processes for their preparation. The compounds are suitable for the treatment and/or prevention of disorders of fatty acid metabolism and glucose utilization disorders as well as of disorders in which insulin resistance is involved.

17 Claims, No Drawings

7-AZAINDOLES, PHARMACEUTICAL COMPOSITIONS AND THEIR THERAPEUTIC APPLICATIONS

CROSS-REFERENCE TO RELATED APPLICATIONS

This application is a continuation of International Patent Application No. PCT/EP2005/009269 filed on Aug. 27, 2005 which is incorporated herein by reference in its' entirety which also claims the benefit of priority of European Patent Application No. 04/021667.3 filed on Sep. 11, 2004.

FIELD OF THE INVENTION

The present invention relates generally to compounds and compositions for the treatment of metabolic diseases and specifically, the present invention relates to compounds that therapeutically modulation and control lipid and/or carbohydrate metabolism and are thus suitable for the prevention and/or treatment of diseases such as type 2 diabetes, atherosclerosis, and the diverse manifestations thereof. Even more specifically, the present invention relates to 7-azaindoles, their physiologically acceptable salts and functional derivatives thereof that exhibit a high degree of peroxisome proliferator-activated receptors (PPAR) agonist activity.

BACKGROUND OF THE INVENTION

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

PPAR agonists are well known and have been described in the prior art, see U.S. Pat. No. 6,200,995 to De La Brouse-Elwood et. al.; WO 03/043997 to Johnston et. al. and WO 01/00603 and WO 02/092590 to Keil et. al.). comprising an oxadiazolone feature as inhibitors of factor Xa were disclosed in DE 101 12 768 A1 and oxodiazolones have also been described as oral hypoglycemic agents in WO 96/13264. PPAR agonists have also been described in the prior art in WO 01/00603 and WO 02/092590 whereas azaindoles are described in WO04/074284, all of which are incorporated by reference herein.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Strict. Funk., 1993, 18(5), 267-77) all of which are incorporated herein by reference.

In humans, PPARgamma exists in three variants, PPARgamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog. Horm. Res., 2001, 56, 239-63; Moller, D. E. and Berger, J. P., Int J Obes Relat Metab Disord., 2003, 27 Suppl 3,17-21; Ram, V. J., Drugs Today, 2003, 39(8),609-32) all of which are incorporated herein by reference. Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. 30 Sci., 2001, 98, 5306-5311). The dual PPARdelta/PPARalpha agonist YM-16638 significantly lowers plasma lipids in rhesus and cynomoigus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang, Y-X. et al., Cell, 2003, 113, 159-170; Luquet, S. et al., FASEB J., 2003, 17, 209-226 ; Tanaka, T. et al., PNAS, 2003, 100, 15924-15929; Holst, D. et al., BioChem. Biophys. Acta, 2003,1633, 43-50; Dressel, U. et al., Mol. Endocrin., 2003, 17, 2477-2493; Lee, C. H. et al., Science, 2003, 302, 453-457). Besides its actions as a regulator of the lipid-, glucose- and cholesterol-metabolism PPARdelta is known to play a role in embryonic development, i.e., implantation and bone formation (Lim, H. and Dey, S. K., Trends Endocrinol Metab., 2000, 11(4),137-42; Ding, N. Z. et al., Mol Reprod Dev., 2003, 66(3), 218-24; Mano, H. et al., J Biol Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol Biol., 2003, 85(2-5), 257-65; Tan, N. S. et al., Am J Clin Dermatol., 2003, 4(8), 523-30; Wahli, W., Swiss Med Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33,194-204). Thus, PPARdelta activators may be of use for the treatment of demyelinating and dysmyelinating diseases.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J.C. et al., 2001, Pharmacological Research, 44(5), 345-52; Kersten, S. et al., Nature, 2000, 405, 421-424; Torra, I. P. et al., Curr Opin Lipidol, 2001,12, 245-254).

The present invention is based on the object of providing compounds which permit therapeutically utilizable modulation of lipid and/or carbohydrate metabolism and are thus suitable for the prevention and/or treatment of diseases such as type-2 diabetes and atherosclerosis and the diverse disease states thereof. The present invention comprises a novel series of compounds which modulate the activity of PPAR receptors responsible for the aforementioned metabolic activity. The disclosed and claimed compounds herein are suitable, in particular, for activating PPARdelta and PPARalpha receptor sites, however, the extent of the relative activation can vary depending on the specific compounds.

SUMMARY OF THE INVENTION

The present invention relates generally to compounds and compositions for the treatment of metabolic diseases and specifically, the present invention relates to compounds that therapeutically modulation and control lipid and/or carbohydrate metabolism and are thus suitable for the prevention and/or treatment of diseases such as type 2 diabetes, atherosclerosis, and the diverse manifestations thereof. The present invention relates to 7-azaindoles, their physiologically acceptable salts and functional derivatives thereof that exhibit a high degree of peroxisome proliferator-activated receptors (PPAR) agonist activity. Compounds of the present invention are described by formula I:

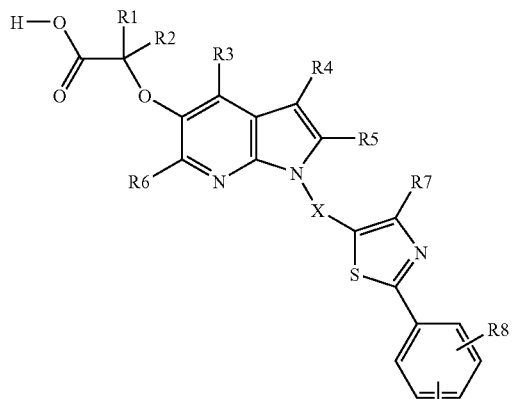

Formula I wherein the respective R-groups are defined herein.

DETAILED DESCRIPTION OF THE INVENTION

This invention relates further to the use of 7-azaindoles, their physiologically acceptable salts and functional derivatives of formula I and their pharmaceutical compositions as peroxisome proliferator-activated receptors (PPAR) ligands. The PPAR ligands of the invention are suitable as modulators of PPAR activity. The 7-azaindole compounds of the present invention are represented by that set forth as formula I

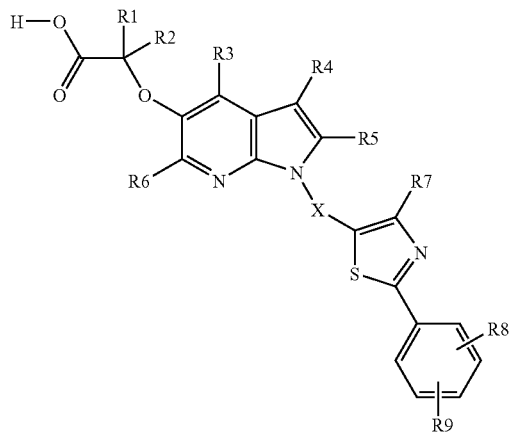

Formula 1 wherein:

R1 and R2 are independently H or (C1-C6)-alkyl, or R1 and R2 taken together with the carbon atom to which they are attached form a (C3-C6)-cyclically;

R3 is selected from the group consisting of H, F, Cl, Br, NO2, CN, CF3, SCH3, (C1-C6)-alkyl, (C2-C6)-alkenyl, and (C1-C4)-alkylene-O—(C1-C4)-alkyl R4 is a H or a (C1-C6)-alkyl, R5 is a H or a (C1-C6)-alkyl, phenyl-;

R6 is selected from the group consisting of H, F, Cl, Br, CN, CF3, SCH3, (C1-C6)-alkyl, and (C1-C4)-alkylene-O—(C1-C4)-alkyl;

R7 is selected from the group consisting of (C1-C6) alkyl, (C1-C4) alkylene-O—(C1-C4)alkyl, (C1-C6)alkylene-phenyl, (C1-C4) alkylene-O—(C1-C4)alkylene-phenyl, (C3-C6)cycloalkyl, (C2-C6) alkenyl, phenyl, O-phenyl, (C1-C6)alkylene-S(O)$_n$—(C1-C6)alkyl, (C1-C6)alkylene-NR10R11, (C1-C6) alkylene-CONR10OR11, (C1-C6)alkylene-SO2NR10R11, (C1-C6)alkylene-NR10SO2-(C1-C6) alkyl, (C1-C6)alkylene-OCONR10R11, (C1-C6) alkylene-NR10COR11 and (C1-C6) alkylene-NR10CONR11 where alkyl may substituted with one or more fluorine or phenyl atoms and where n may be 0, 1 or 2;

R8 and R9 are independently selected from the group consisting of H, F, Cl, Br, CF$_3$, OCF$_3$, (C$_1$-C$_6$)-alkyl, O—(C$_1$-C$_6$)-alkyl, SCF$_3$, SF$_5$, OCHF$_2$, OCH$_2$F, OCF$_2$-CHF$_2$, and O-phenyl, OH, NO$_2$;

R10 and R11 are H, (C1-C6)-alkyl or (C3-C6)-cycloalkyl optionally substituted with one to three F or heteroaryl; optionally R10 and R11 may together with the N atom to which they are attached form a 4, 5 or 6-membered saturated, partly saturated or unsaturated heterocycle wherein a carbon (C) atom may be replaced by N, O, S, SO and SO$_2$;

X is —CH2- or —CH2CH2-; and, a pharmaceutically acceptable salt thereof.

Preferably, the compounds of the present invention comprise a formula I wherein phenyl is substituted by R9 only. More preferably, the compounds of the present invention comprise a formula I wherein R9 is in the para-position. Even more preferably, the compounds of the present invention comprise formula I wherein one or more of the substituents has the following meaning R1 and R2 is H;

R3 is H, (C1-C6)-alkyl;

R4 is H;

R5 is H;

R6 is H;

alkylene-O—(C1-C4) alkyl, (C1-C6) alkylene-phenyl, (C1-C4) alkylene-O—(C1-C4)alkylene-phenyl, (C3-C6)cycloalkyl, (C2-C6)alkenyl, phenyl, O-phenyl, (C1-C6)alkylene-S(O)$_n$—(C1-C6)alkyl, (C1-C6) alkylene-NR10R11, (C1-C6)alkylene-CONR10R11, (C1-C6)alkylene-SO2NR10R11

R7 is independently selected from the group consisting of (C1-C6)alkyl, (C1-C4), (C1-C6)alkylene- NR10SO2-(C1-C6)alkyl, (C1-C6)alkylene-OCONR10R11, (C1-C6)alkylene-NR10COR11, (C1-C6)alkylene-NR10CONR11 where alkyl may substituted with one or more fluorine or phenyl atoms and wherein optionally n may be 0, 1 or 2;

R8 is H;

R9 is CF$_3$;

R10 and R11 are H, (C1-C6)-alkyl or (C3-C6)-cycloalkyl optionally substituted with one to three F or heteroaryl groups and optionally R10 and R11 may, together with the N atom to which they are attached, form together with the N atom to which they are attached a 4, 5 or 6-membered heterocycle wherein a C atom may be replaced by N, O, S, SO, SO$_2$. and X is —CH2-.

Most preferably, the compounds of the formula are those wherein one or more of the substituents has the following meaning R1 and R2 are H;

R3 is H or (C1-C6)-alkyl;

R4 is H;

R5 is H;

R6 is H;

R7 is independently selected from the group consisting of (C1-C6) alkyl, (C1-C4) alkylene-O—(C1-C4) alkyl, (C1-C6) alkylene-phenyl, (C1-C4) alkylene-O—(C1-C4) alkylene-phenyl, (C3-C6) cycloalkyl, (C2-C6) alkenyl, phenyl and O-phenyl, where alkyl may substituted with one or more fluorine or phenyl atoms and where n may be 0, 1 or 2;

R8 is H;

R9 is CF$_3$;

X is —CH2-.

Most preferably, the compounds of the present invention comprise those of formula 1, 5 wherein R1, R2, R5 and R6 are H;

R3 is H or (C1-C6)-alkyl;

R4 is H;

R7 is (C1-C6)-alkyl;

R8 is CF3;

R9 is H;

X is —CH$_2$—.

This invention also encompasses all combinations of preferred aspects of the invention described herein.

The alkyl and alkenyl radicals in the substituents R1, R2, R3, R4, R5, R6, R7, R8, R9, R10 and R11 may be either straight-chain or branched and may be substituted by from one to four fluorine atoms.

Unless otherwise indicated the term heteroaryl refers to aromatic, mono- or bicyclic rings having 4 to 11 carbon atoms, wherein at least one carbon atom is replaced by a heteroatom selected from the group consisting of N, O or S.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by known methods even if not specifically described in some cases.

Compounds of this type are particularly suitable for the treatment and/or prevention of:

1. —Disorders of fatty acid metabolism and glucose utilization disorders.

Disorders in which insulin resistance is involved

2. Diabetes mellitus, especially type-2 diabetes, including the prevention of the diseased manifestations associated therewith.

Particular aspects in this connection are hyperglycemia, improvement in insulin resistance, improvement in glucose tolerance, protection of the pancreatic B3 cells prevention of macro- and microvascular disorders 3. Dyslipidemias and their diseased manifestations such as, for example, atherosclerosis, coronary heart disease, cerebrovascular disorders etc, especially those (but not restricted thereto) which are characterized by one or more of the following factors:

high plasma triglyceride concentrations, high postprandial plasma triglyceride concentrations,
low HDL cholesterol concentrations
low ApoA lipoprotein concentrations
high LDL cholesterol concentrations
small dense LDL cholesterol particles
high ApoB lipoprotein concentrations
4. Various other conditions which may be associated with the metabolic syndrome, such as:
obesity (excess weight), including central obesity
thromboses, hypercoagulable and prothrombotic states (arterial and venous)
high blood pressure
heart failure such as, for example (but not restricted thereto), following myocardial infarction, hypertensive heart disease or cardiomyopathy
5. Disorders or conditions in which inflammatory reactions are involved:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
asthma
lupus erythematosus (LE) or inflammatory rheumatic disorders such as, for example, rheumatoid arthritis
other inflammatory states
6. Disorders of cell cycle or cell differentiation processes:
adipose cell tumors
lipomatous carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis
7. CNS disorders, neurodegenerative disorders and/or demyelinating disorders:
Alzheimer's disease
multiple sclerosis
Parkinson's disease
adrenoleukodystrophy (ALD)
adrenomyeloneuropathy
AIDS-vacuolar myelopathy
HTLV-associated myelopathy
Leber's hereditary optic atrophy
progressive multifocal leukoencephalopathy (PML)
subacute sclerosing panencephalitis
Guillian-Barre syndrome
tropical spastic paraparesis
acute disseminated encephalomyelitis (ADEM)
acute viral encephalitis
acute transverse myelitis
spinal cord and brain trauma
Charot-Marie-Tooth disease
8. Skin disorders and/or disorders of wound healing processes:
erythemato-squamous dermatoses such as, for example, psoriasis
acne vulgaris
other skin disorders and dermatological conditions which are modulated by PPAR
eczemas and neurodermitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, Lichen planus
skin cancer such as, for example, basal-cell carcinomas, melanomas or cutaneous T-cell lymphomas
localized benign epidermal tumors such as, for example, keratoderma, epidermal naevi
chilblains
wound healing
9. Other disorders
high blood pressure
pancreatitis
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in non-therapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example sub-cutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, slow-dissolving oral tablets or tablets, each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving oral tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations With Other Pharmaceutical Actives

The compounds of the invention can be administered alone or in combination with one or more further pharmacologically active substances which have, for example, favorable effects on metabolic disorders as well. Examples of such actives are:
1. pharmaceutical actives which lower blood glucose, i.e., anti-diabetics,
2. active ingredients for the treatment of dyslipidemias,
3. anti-atherosclerotic actives
4. anti--obesity agents,
5. anti-inflammatory active ingredients
6. active ingredients for the treatment of malignant tumors
7. anti-thrombotic active ingredients
8. pharmacological actives for the treatment of high blood pressure
9. actives for the treatment of heart failure and
10. active for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples of additional suitable actives useful in the pharmaceutical combinations of the present invention are:

Anti-diabetics

Suitable anti-diabetics are disclosed for example in the Rote Liste 2001, chapter 12 or in the USP Dictionary of USAN and International Drug Names, US Pharmacopeia, Rockville 2001. Anti-diabetics include all insulins and insulin derivatives such as, for example, Lantus® (see www.lantus.com) or Apidra®, and other fast-acting insulins (see U.S. Pat. Nos. 6,221,633 and 6,225,310 both to Ertl et. al. ), GLP-1 receptor modulators as described in WO 01/04146 or else, for example, those disclosed in U.S. Pat. No. 6,268,343 to Knudsen et. al. Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in U.S. Pat. No. 5,889,002 to Neilsen et. al. and Ertl et. al. '633, insulin sensitizers, inhibitors of liver enzymes involved in the stimulation of gluconeogenesis and/ or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in WO 2004/007517, WO 2004/052902, and WO 2004/052903.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and mefformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. Nos. 6,245, 744, 6,221,897, 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001

September-October), 18(5), 230-6.) Caromax is a carob-containing product from Nutrinova, Nutrition Specialties & Food Ingredients GmbH, Industriepark Höechst, 65926 Frankfurt-Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In another embodiment of the invention, the compounds of the formula I are administered in combination with a fibrate such as, for example, fenofibrate, gemfibrozil, clofibrate, bezafibrate.

In another embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In another embodiment of the invention, the compounds of the formula I are administered in combination with an ATP citrate lyase inhibitor.

In yet another embodiment of the invention, the compounds of the formula I are administered in combination with a squalene synthetase inhibitor.

In one embodiment of the invention, the compounds of the formula I are administered in combination with a lipoprotein (a) antagonist.

Anti-obesity Agents

In one embodiment of the invention, the compounds of the formula I are administered in combination with a lipase inhibitor such as, for example, orlistat.

In another embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazole-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the scope of the claims of the present invention. The examples detailed below are provided to better The activity of the compounds was tested as follows:

Determination of EC50 Values of PPAR Agonists In the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fafty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession #AF264724) were cloned in 5'-upstream of a 68 bp-long minimal MMTV promoter (Accession #V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Accession #M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol.1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARalpha receptor (amino acids S167-Y468; Accession #S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#353112, Becton Dickinson) in a cell culture incubator at 37° C. in the presence of 5% $CO_2$. The 80%-confluent cells are washed once with 15 ml of PBS (#14190-094, invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, invitrogen) and the previously described antibiotics (zeocin, G418, penicillin and streptomycin). Test substances are tested in 11 different concentrations in the range from 10 μM to 100 pM. More potent compounds are tested in concentration ranges from 1 μM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 μl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

Principle

The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanPPARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion tothe GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARdelta receptor (amino acids S139-Y441; Accession #L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

The potency of the described examples are indicated in the following table:

| Example | PPARalpha EC50 (µM) | PPARdelta EC50 (µM) |
|---|---|---|
| 1 | 0.04 | 0.47 |
| 2 | 0.32 | 0.14 |

The examples given in Table I serve to illustrate the invention, but without limiting it.

TABLE I

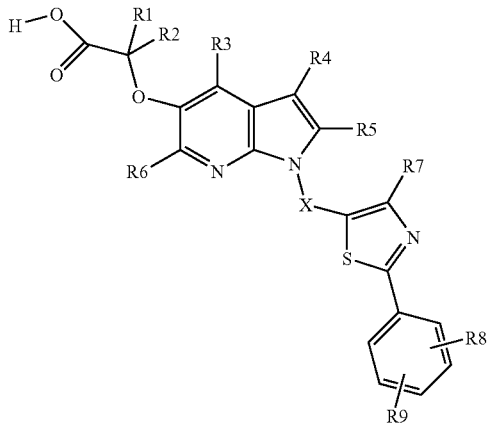

where R1 = R2 = R4 = R5 = R6 = H.

| example | R3 | R7 | R8 | R9 | X |
|---|---|---|---|---|---|
| 1 | —H | —CH2—CH2—CH2—CH3 | p-CF3 | H | —CH2— |
| 2 | —CH2—CH2—CH3 | —CH2—CH2—CH2—CH3 | p-CF3 | H | —CH2— |

Processes

The compounds of the general formula I according to the invention can be obtained as outlined to the reaction schemes below:

Process A:

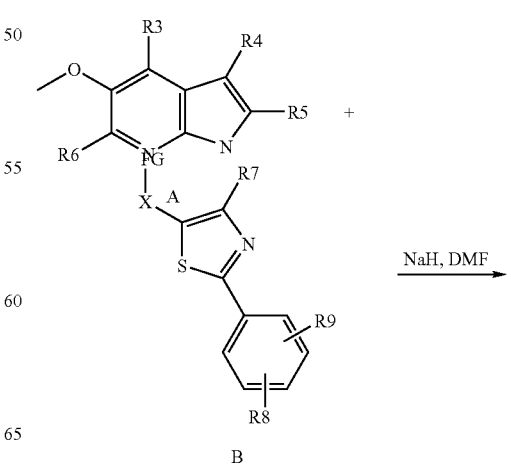

B

-continued

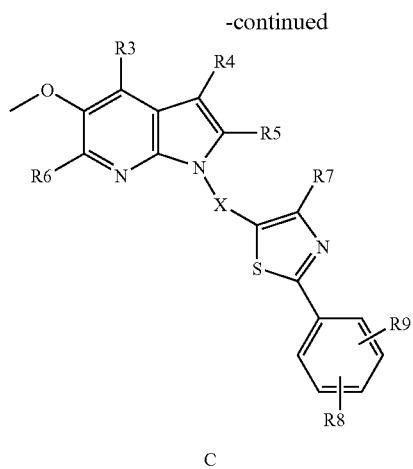

C

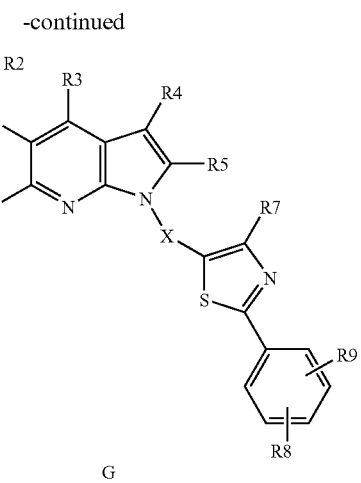

G

A 5-Methoxy-7-azaindole of the general formula A, where R3,R4,R5 and R6 are as defined above is reacted with a phenylthiazole-methylhalide or -mesylate or -tosylate of general formula B, where X, R7, R8 and R9 are as defined above, in presence of a base, e.g. sodium hydride in a solvent as dimethylformamide to give a compound of the general formula C.

The compound of the general formula C is converted to the product of general formula D by reaction with borontribromide in a solvent as dichloromethane. The compound of the general formula D is reacted with a bromoacetic acid derivative of general formula E where R1 und R2 are as defined above in presence of a base as cesium carbonate in a polar aprotic solvent as dimethylformamide to give a compound of the general formula F. The compound of general formula F is converted to a compound of general formula G upon treatment with an acid as trifluoro-acetic acid in an apolar solvent such as dichloromethane.

Example 1 was obtained according to process A.
Other compounds can be obtained accordingly or by processes known in the art.
Process B:

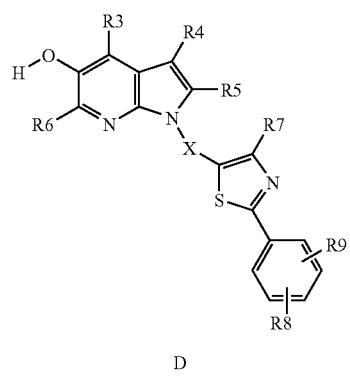

D

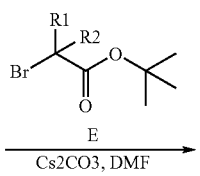

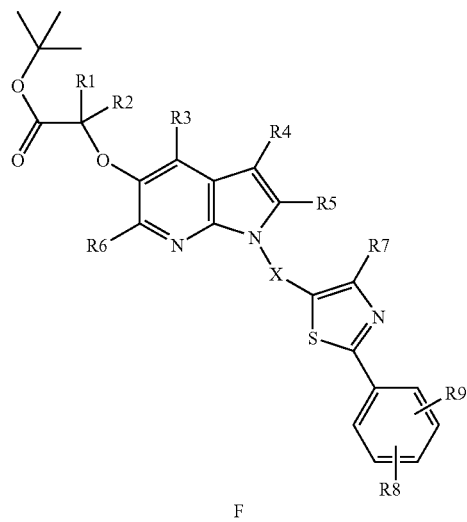

F

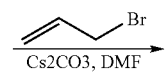

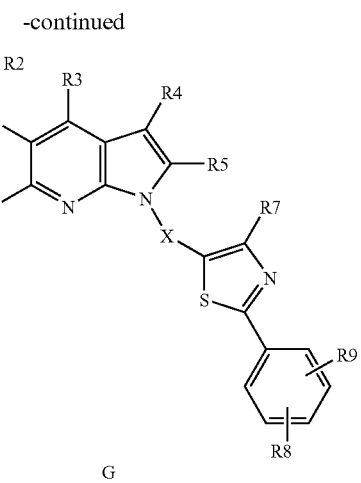

D

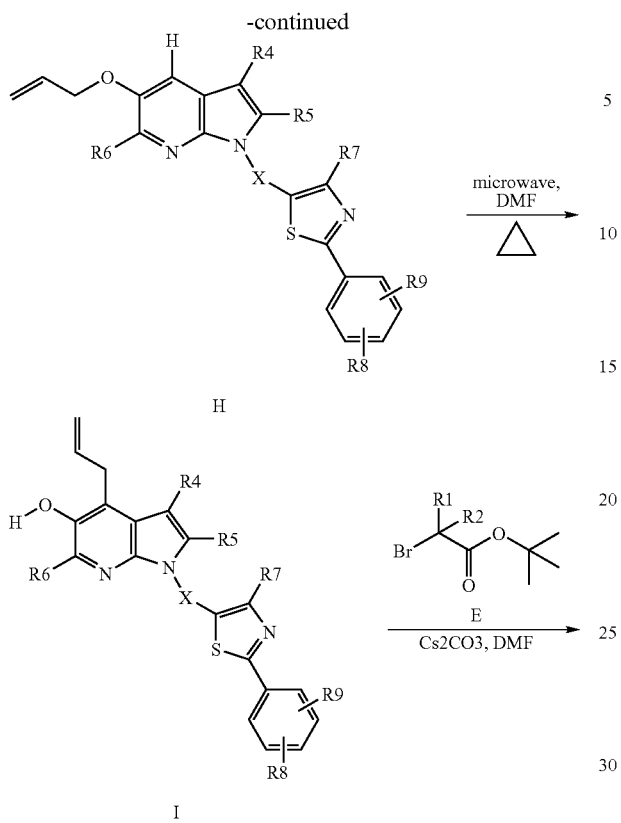
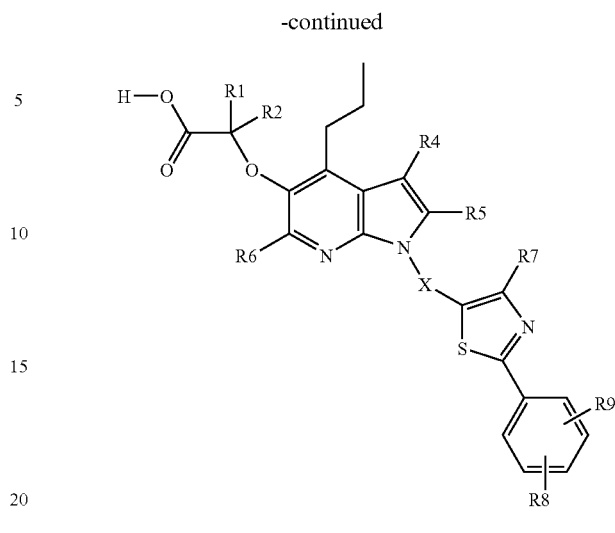

The compound of general formula D where R3=H and R4, R5, R6, R7, R8, R9 and X are as defined above is reacted with allylbromide in the presence of a base as cesium carbonate in a polar aprotic solvent as dimethylformamide to give a compound of general formula H. The compound of general formula H is rearranged to a compound of general formula I upon heating, e.g. in a microwave. The compound of the general formula I is reacted with a bromoacetic acid derivative of general formula E where R1 and R2 are defined above in presence of a base as cesium carbonate in a polar aprotic solvent as dimethylformamide to give a compound of the general formula K. The compound of general formula K is converted to a compound of general formula L upon treatment with an acid as trifluoro-acetic acid in an apolar solvent as dichloromethane. The compound of general formula L is converted to a compound of general formula M upon treatment with hydrogen in the presence of a catalyst as palladium.

Example 2 was obtained according to process B.

Other compounds can be obtained accordingly or by known processes.

Process C:

This process is used for synthesizing the building block B where X=CH2 and R7, R8 and R9 are as defined above.

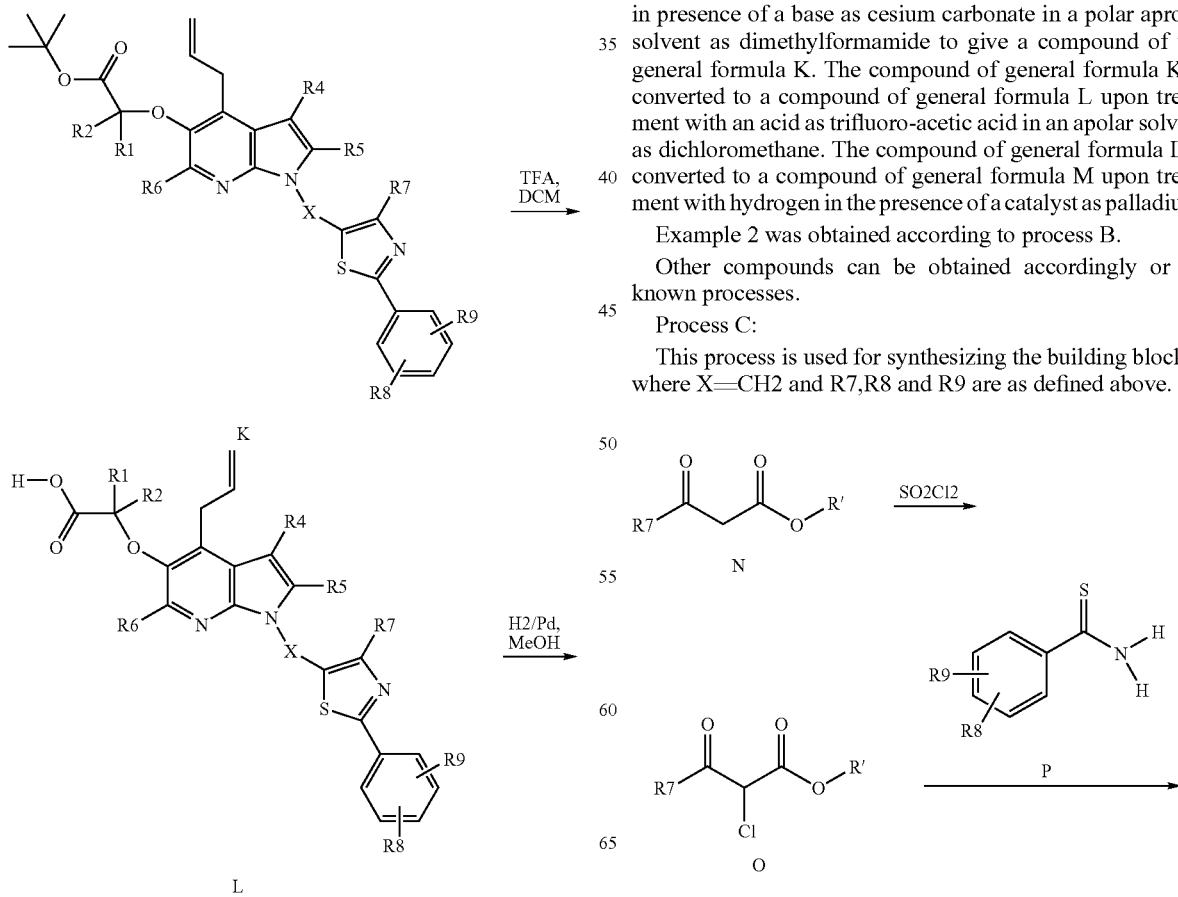

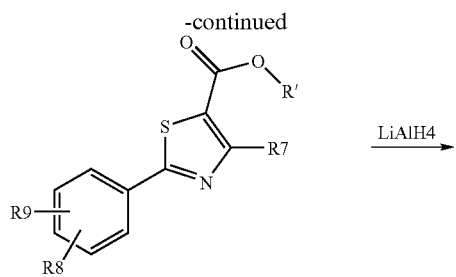

Q

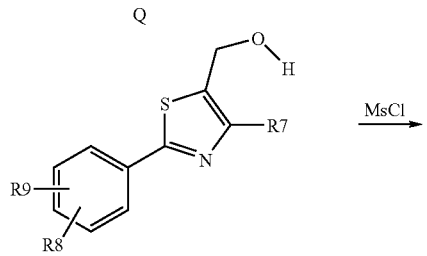

R

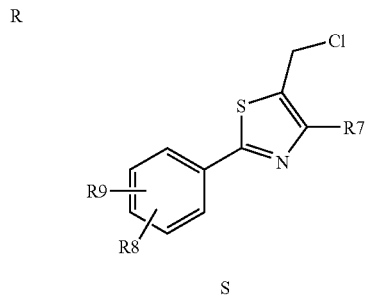

S

R' = methyl or ethyl

A 3-Oxo-butyric acid methyl- or ethyl ester of general formula N where R7 is as defined above is reacted with sulfuryl chloride to a chlorine substituted compound of general formula O. This compound of general formula O is reacted with a thiobenzamide of general formula P, where R8 and R9 are as defined above to obtain a phenylthiazole ester of general formula O. The ester of general formula Q is reduced with a reducing agent ,e.g. lithium aluminum hydride, to the alcohol of general formula R. The alcohol of general formula R is reacted with methanesulfonyl chloride in the presence of a base as triethylamine in a solvent as dichloromethane to obtain the building block of general formula S.

Other compounds can be obtained accordingly or by known processes.

List of Abbreviation:

| Ac | acetyl |
| Bn | benzyl |
| iBu | isobutyl |
| tBu | tert-Butyl |
| BuLi | n-butyllithium |
| Bz | benzoyl |
| Cy | cyclohexyl |
| DC | Thin layer chromatography |
| DCI | Direct chemical ionization (MS) |
| DCM | dichloromethane |
| DMAP | N,N-dimethylaminopyridine |
| DMF | N,N-dimethylformamide |
| DMSO | dimethylsulfoxide |
| EE | ethyl acetate |
| eq | equivalents |
| ESI | electronspray-Ionisation (MS) |
| FG | Leaving group |
| Hal | halogen |
| HPLC | High performance liquid chromatography |
| LC-MS | liquid chromatography coupled with mass-spectroscopy |
| Me | methyl |
| MS | mass-spectroscopy |
| MsCl | Methansulfonylchloride |
| NMR | Nuclear magnetic resonance |
| p | para |
| Pd/C | palladium on carbon |
| iPr | isopropyl |
| nPr | n-propyl |
| Rf | retention time (DC) |
| tert | tertiary |

Further compounds of the formula I can be prepared correspondingly or by known processes.

The experimental procedures for preparing the examples mentioned above are described below:

Building Block Synthesis According to Process C:

4-Butyl-5-chloromethyl-2-(4-trifluoromethyl-phenyl)-thiazole

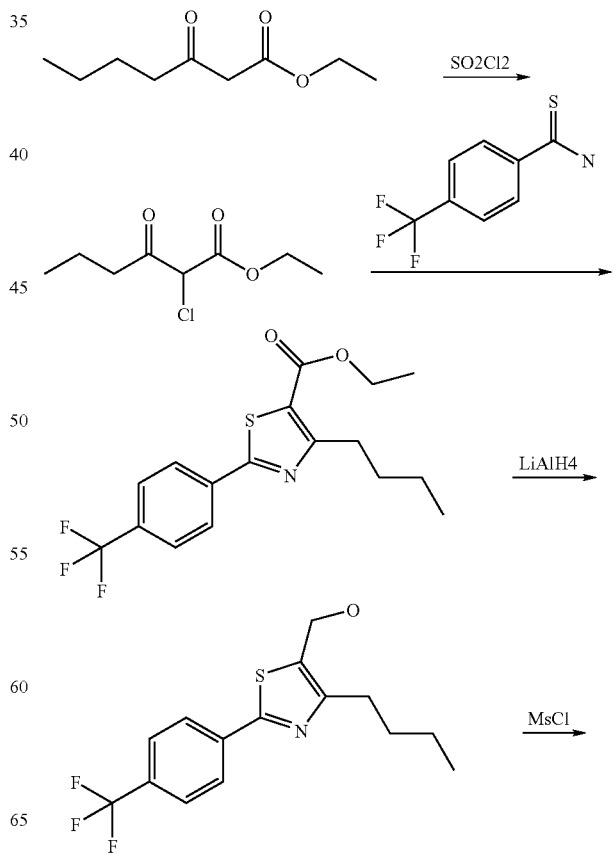

4-Butyl-2-(4-trifluoromethyl-phenyl)-thiazol-5-carboxylic acid methyl ester

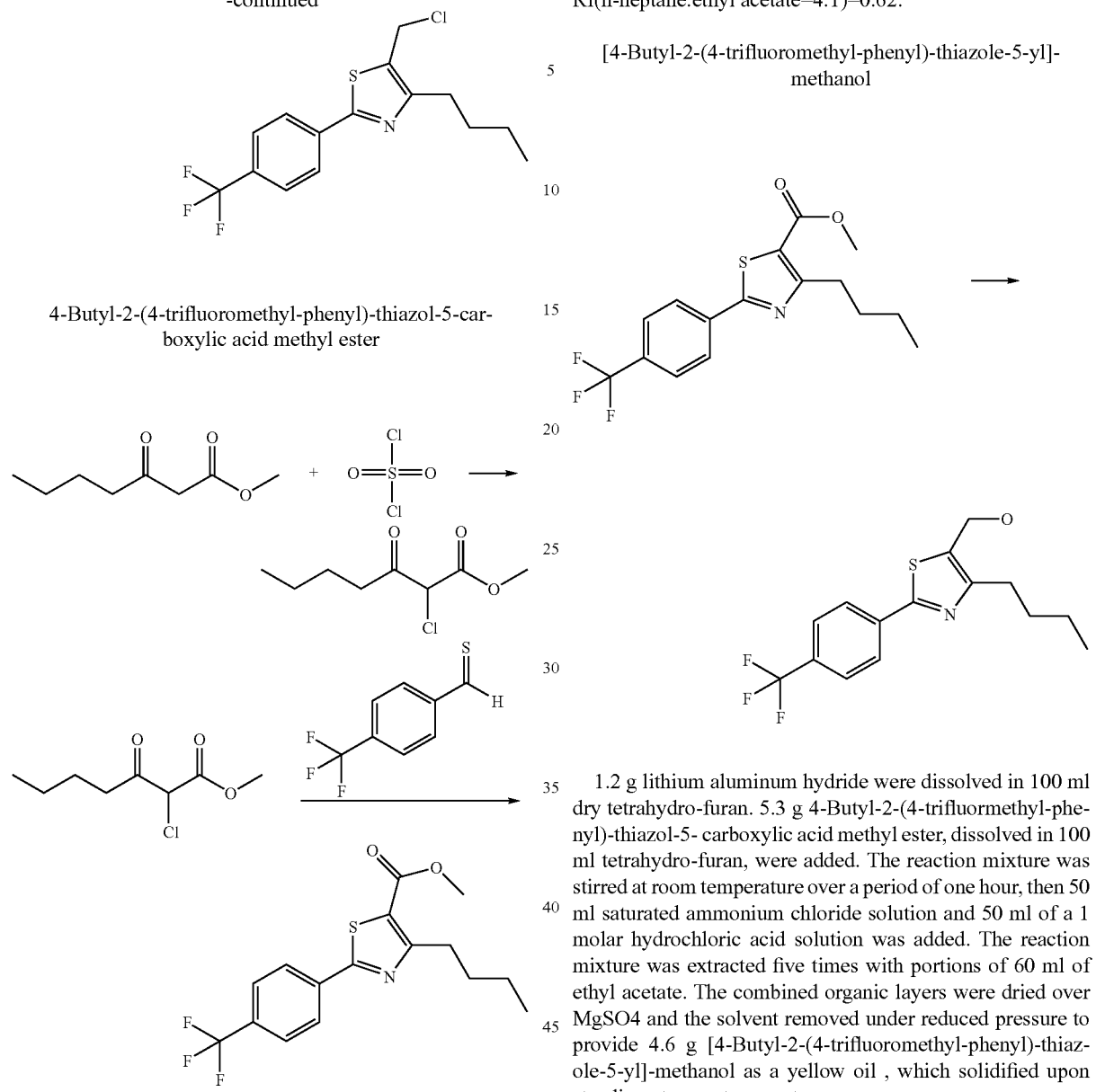

5.0 g 3-Oxo-heptanoic acid methyl ester were dissolved in 80 ml dry dichloromethane and 2.82 ml sulfurylchloride were added. The reaction mixture was stirred at room temperature for 30 minutes. 20 ml of water were added and the reaction mixture extracted five times with portions of 30 ml of dichloromethane. The combined organic extracts were washed with water and saturated NaHCO3 solution and brine and dried over MgSO4. The solvent was removed under reduced pressure to obtain 6.0 g 2-Chloro-3-oxo-heptanoic acid methyl ester as raw material. This material was used without further purification. 6.0 g 2-Chloro-3-oxo-heptanoic acid methyl ester were dissolved in 50 ml ethanol and 6.4 g 4-(Trifluoromethyl)thiobenzamide were added. The reaction mixture was heated under reflux overnight. The solvent was removed under reduced pressure and the residue purified by chromatography with the eluent n-heptane:ethyl acetate=100:1=>60:1. This gives 7.4 g 4-Butyl-2-(4-trifluoromethylphenyl)-thiazol-5- carboxylic acid methyl ester as yellow oil.

C16H16F3NO2S (343.37), MS(ESI): 344.1 (M+H+), Rf(n-heptane:ethyl acetate=4:1)=0.62.

[4-Butyl-2-(4-trifluoromethyl-phenyl)-thiazole-5-yl]-methanol 1.2 g lithium aluminum hydride were dissolved in 100 ml dry tetrahydro-furan. 5.3 g 4-Butyl-2-(4-trifluormethyl-phenyl)-thiazol-5- carboxylic acid methyl ester, dissolved in 100 ml tetrahydro-furan, were added. The reaction mixture was stirred at room temperature over a period of one hour, then 50 ml saturated ammonium chloride solution and 50 ml of a 1 molar hydrochloric acid solution was added. The reaction mixture was extracted five times with portions of 60 ml of ethyl acetate. The combined organic layers were dried over MgSO4 and the solvent removed under reduced pressure to provide 4.6 g [4-Butyl-2-(4-trifluoromethyl-phenyl)-thiazole-5-yl]-methanol as a yellow oil , which solidified upon standing at room temperature.

C15H16F3NOS (315.36), MS(ESI): 316.4 (M+H+).

4-Butyl-5-chloromethyl-2-(4-trifluoromethyl-phenyl)-thiazole

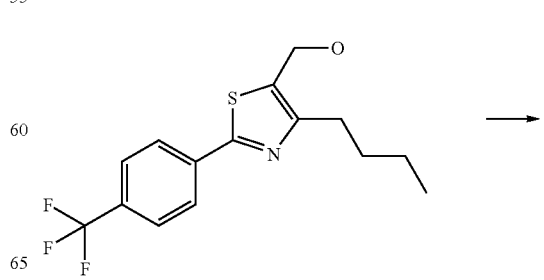

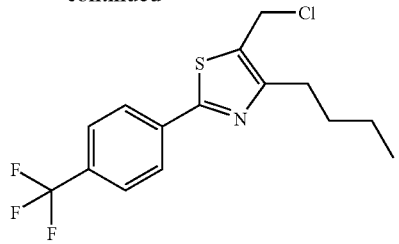

1.0 g [4-Butyl-2-(4-trifluoromethyl-phenyl)-thiazole-5-yl]-methanol were dissolved in 50 ml dichloromethane, 0.88 ml triethylamine and 0.39 ml methanesulfonyl chloride were added. The reaction mixture was stirred at room temperature for a period of three hours then 100 ml of dichloromethane were added and the reaction mixture washed with 50 ml of saturated NaHCO3 solution , water and brine. The organic layer was dried over MgSO4 and the solvent removed under reduced pressure. This provided 1.0 g 4-Butyl-5-chloromethyl-2-(4-trifluoromethyl-phenyl)-thiazole as yellow oil.

C15H15ClF3NS (333.81), MS(ESI): 334.3 (M+H$^+$).

EXAMPLE 1

{1-[4-Butyl-2-(4-trifluoromethyl-phenyl)-thiazol-5-ylmethyl]-1H-pyrrolo[2,3-b]pyridin-5-yloxy}-acetic acid

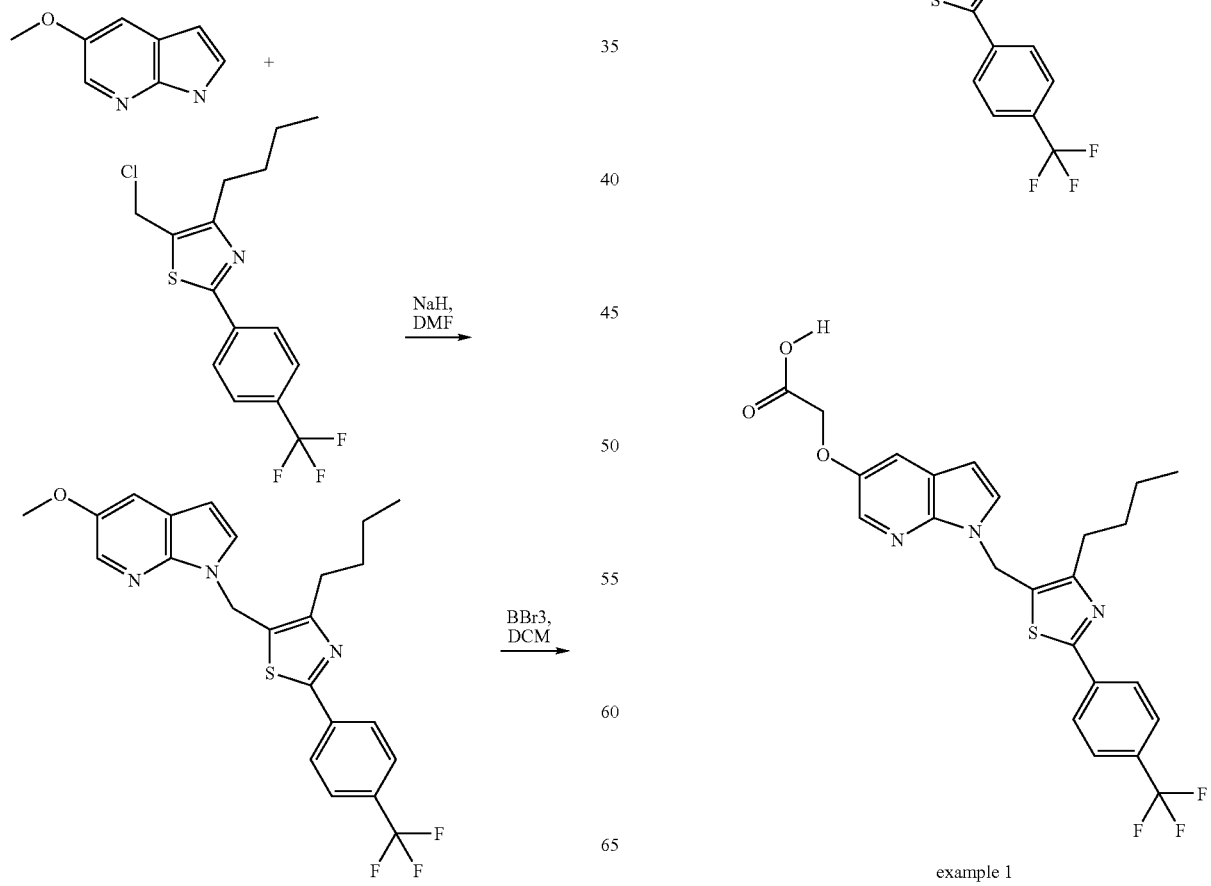

example 1

1-[4-Butyl-2-(4-trifluoromethyl-phenyl)-thiazol-5-ylmethyl]-5-methoxy-1H-pyrrolo[2,3-b]pyridine

1-[4-Butyl-2-(4-trifluoromethyl-phenyl)-thiazol-5-ylmethyl]-1H-pyrrolo[2,3-b]pyridin-5-ol

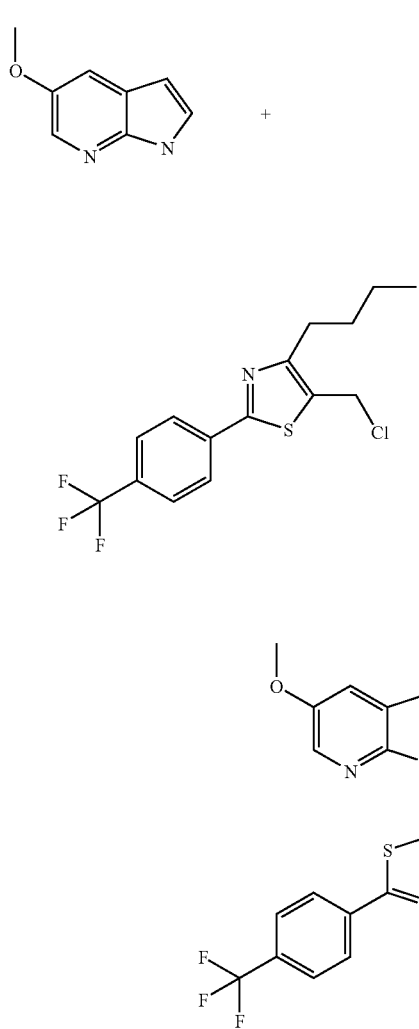

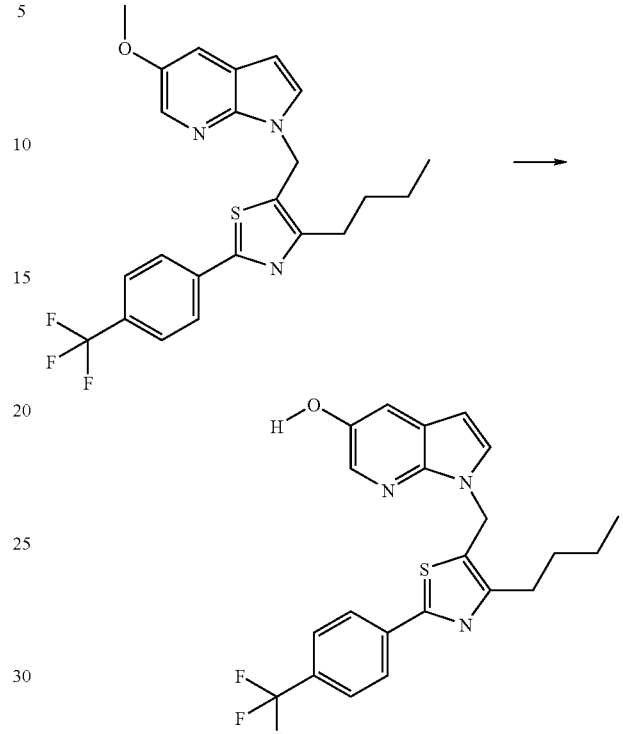

1.10 g 5-Methoxy-1H-pyrrolo[2,3-b]pyridine[1] (impure with 5-Bromo-1H-pyrrolo[2,3-b]pyridine) were dissolved in 50 ml dry dimethylformamide. 890 mg of a 60% suspension of sodium hydride in mineral oil was added and the reaction mixture was stirred at room temperature for 30 minutes. 2.5 g 4-Butyl-5-chloromethyl-2-(4-trifluoromethyl-phenyl)-thiazole were added and the reaction mixture stirred at room temperature for an additional hour. Then 150 ml ethyl acetate was added and the reaction mixture extracted three times with portions of 20 ml of water and brine. The organic layer was dried over MgSO4 and the solvent removed under reduced pressure. The residue was purified by chromatography with the eluent n-heptane:ethyl acetate=40:1=>20:1 to separate out the byproduct 5-Bromo-1-[4-butyl-2-(4-trifluoromethyl-phenyl)-thiazol-5-ylmethyl]-1H-pyrrolo[2,3- b]pyridine. This provided 950 mg 1-[4-Butyl-2-(4-trifluoromethyl-phenyl)-thiazol-5-ylmethyl]-5-methoxy-1H-pyrrolo[2,3- b]pyridine as yellow solid.

[1] The synthesis of 5-Methoxy-1H-pyrrolo[2,3-b]pyridine is described in HETEROCYCLES, Vol. 50, No.2, 1999 and WO2003/064413.

C23H22F3N3OS (445.51), LCMS(ESI): 446.2(M+H+), Rf(n-heptane:ethyl acetate=10:1)=0.22.

850 mg 1-[4-Butyl-2-(4-trifluoromethyl-phenyl)-thiazol-5-ylmethyl]-5-methoxy-1H-pyrrolo[2,3- b]pyridine was dissolved in 50 ml dichloromethane. At −78° C. 1.90 ml of a 1 molar solution of borontribromide in dichloromethane was added. The reaction mixture was allowed to warm up to room temperature. Then the reaction mixture was heated under reflux for additional two hours. 150 ml ethyl acetate were added and the mixture washed with 50 ml of a one molar solution of hydrochloric acid. The organic layer was dried over MgSO4 and the solvent removed under reduced pressure. The residue was purified by RP-HPLC to provide 930 mg 1-[4-Butyl-2-(4-trifluoromethylphenyl)-thiazol-5-ylmethyl]-1H-pyrrolo[2,3-b]pyridin-5-ol as a lyophilisate.

C22H20F3N3OS (431.48), LCMS(ESI): 432.4(M+H+), Rf(n-heptane:ethyl acetate=5:1)=0.11.

{1-[4-Butyl-2-(4-trifluoromethyl-phenyl)-thiazol-5-ylmethyl]-1H-pyrrolo[2,3-b]pyridin-5-yloxy}-acetic acid

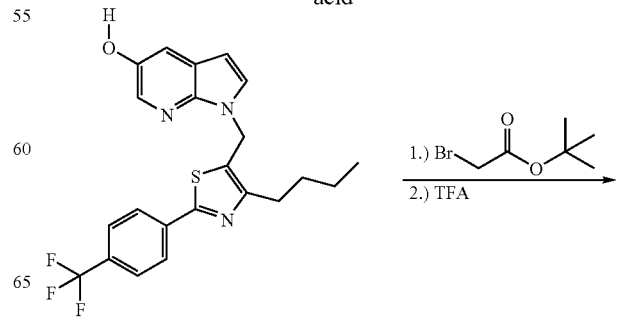

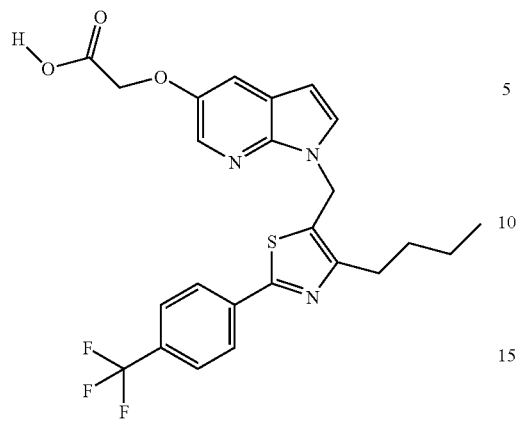

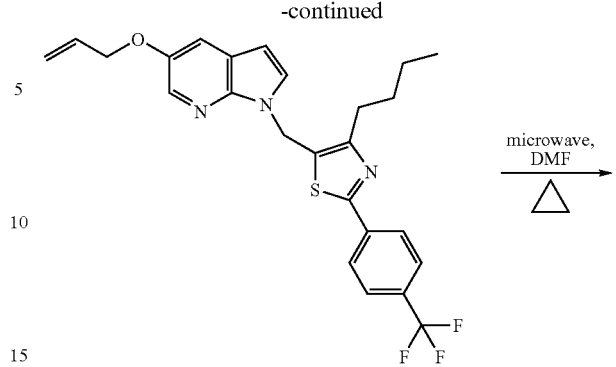

200 mg 1-[4-Butyl-2-(4-trifluoromethyl-phenyl)-thiazol-5-ylmethyl]-1H-pyrrolo[2,3-b]pyridin-5-ol were dissolved in 20 ml dimethylformamide and 300 mg cesium carbonate and 180 mg tert.-butylbromoacetate were added. The reaction mixture was stirred at room temperature for one hour then 100 ml ethyl acetate were added and the mixture was washed five times with portions of 20 ml of water The organic layer was dried over MgSO4 and the solvent removed under reduced pressure. The residue was dissolved in 10 ml dichloromethane and 4 ml trifluoroacetic acid were added. The reaction mixture was stirred at room temperature for three hours then 100 ml toluene were added and the solvents removed under reduced pressure. The residue was purified by RP-HPLC to provide 155 mg {1-[4-Butyl-2-(4-trifluoromethyl-phenyl)-thiazol-5-ylmethyl]-1H-pyrrolo[2,3-b]pyridin-5-yloxy}-acetic acid as lyophilisate.

C24H22F3N3O3S (489.52), LCMS(ESI): 490.2(M+H⁺).

Example 2

{1-[4-Butyl-2-(4-trifluoromethyl-phenyl)-thiazol-5-ylmethyl]-4-propyl-1H-pyrrolo[2,3-b]pyridin-5-yloxy}-acetic acid

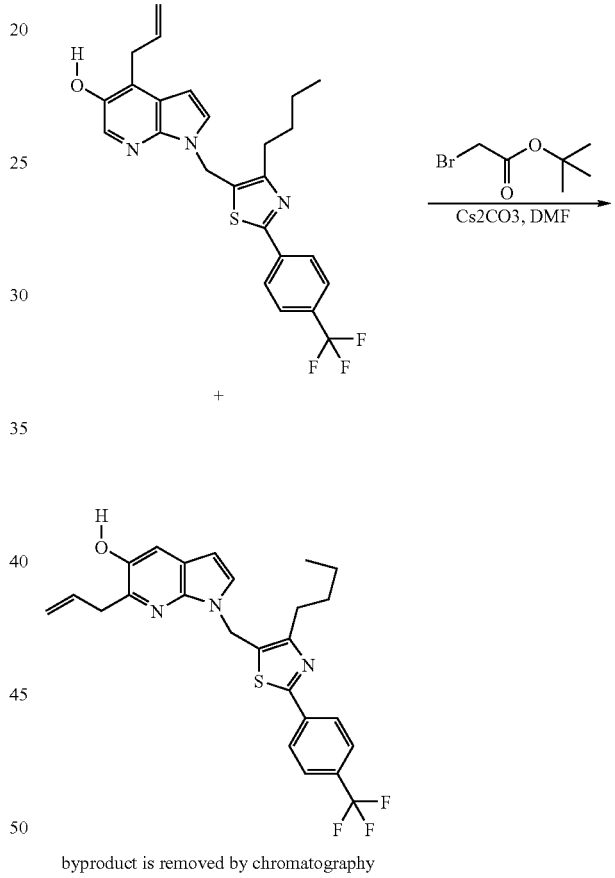

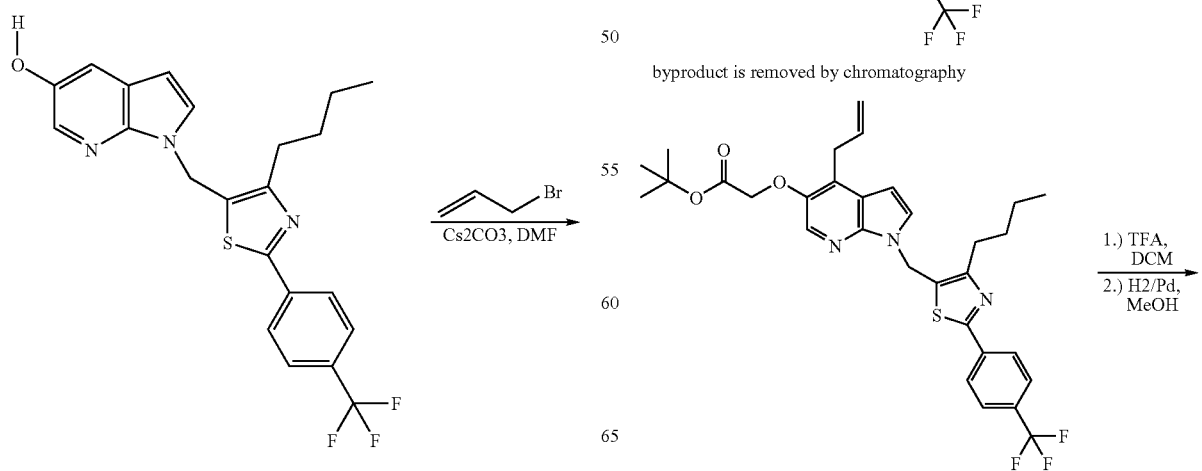

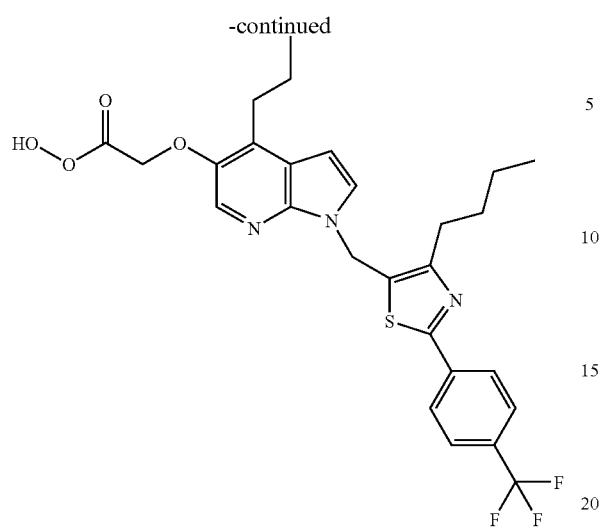

5-Allyloxy-1-[4-butyl-2-(4-trifluoromethyl-phenyl)-thiazol-5-ylmethyl]-1H-pyrrolo[2,3-b]pyridine

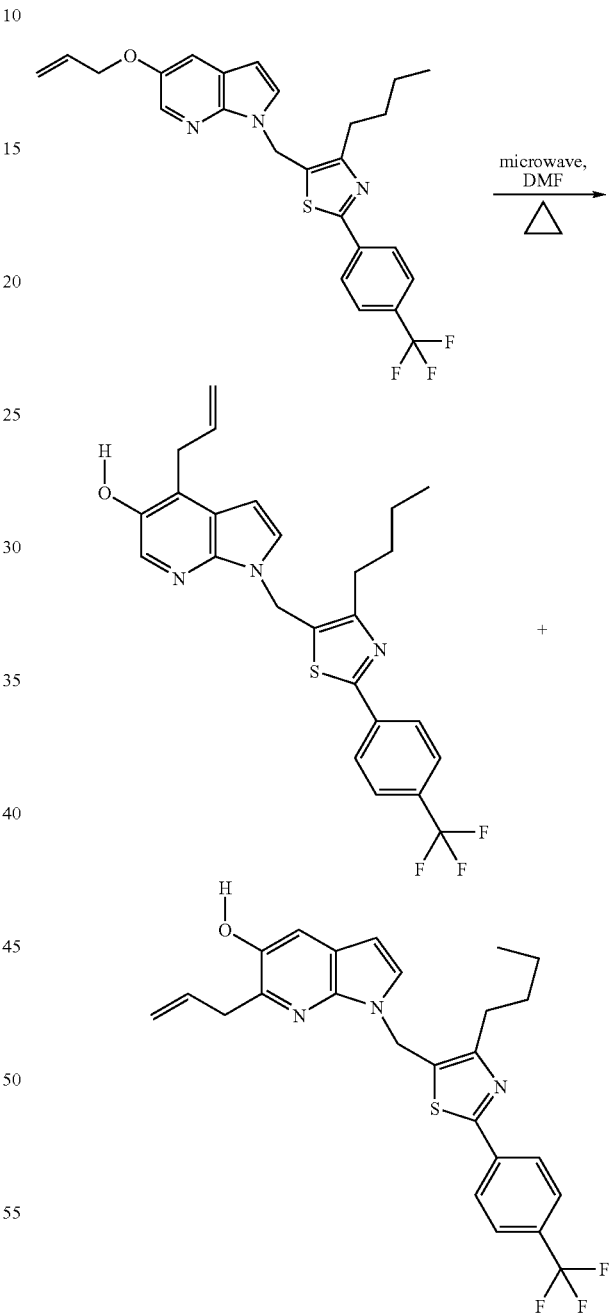

730 mg 1-[4-Butyl-2-(4-trifluoromethyl-phenyl)-thiazol-5-ylmethyl]-1H-pyrrolo[2,3-b]pyridin-5-ol were dissolved in 20 ml dimethylformamide and 1.1 mg cesium carbonate and 410 mg allylbromide were added. The reaction mixture was stirred at room temperature for one hour then 100 ml ethyl acetate were added and the mixture was washed five times with portions of 20 ml of water The organic layer was dried over MgSO4 and the solvent removed under reduced pressure. This gives 800 mg 5-Allyloxy-1-[4-butyl-2-(4-trifluoromethyl-phenyl)-thiazol-5-ylmethyl]-1H-pyrrolo[2,3-b]pyridine as yellow oil.

C25H24F3N3OS (471.55), LCMS(ESI): 472.2 (M+H$^+$).

4-Allyl-1-[4-butyl-2-(4-trifluoromethyl-phenyl)-thiazol-5-ylmethyl]-1H-pyrrolo[2,3-b]pyridin-5-ol 800 mg 5-Allyloxy-1-[4-butyl-2-(4-trifluoromethyl-phenyl)-thiazol-5-ylmethyl]-1H-pyrrolo[2,3-b]pyridine were dissolved in 15 ml dimethylformamide and was stirred under microwave radiation (Personal chemistry/200° C.) for two hours. The cooled mixture was evaporated in vacuo and the resulting crude material was purified by reversed phase HPLC. The byproduct 6-Allyl-1-[4-butyl-2-(4-trifluoromethyl-phenyl)-thiazol-5-ylmethyl]-1H-pyrrolo[2,3-b]pyridin-5-ol was separated to provide 140 mg 4-Allyl-1-[4-butyl-2-(4-trifluoromethyl-phenyl)-thiazol-5-ylmethyl]-1H-pyrrolo[2,3-b]pyridin-5-ol as lyophilisate.

C25H24F3N3OS (471.55), LCMS(ESI): 472.5 (M+H$^+$).

{1-[4-Butyl-2-(4-trifluoromethyl-phenyl)-thiazol-5-ylmethyl]-4-propyl-1H-pyrrolo[2,3-b]pyridin-5-yloxy}-acetic acid

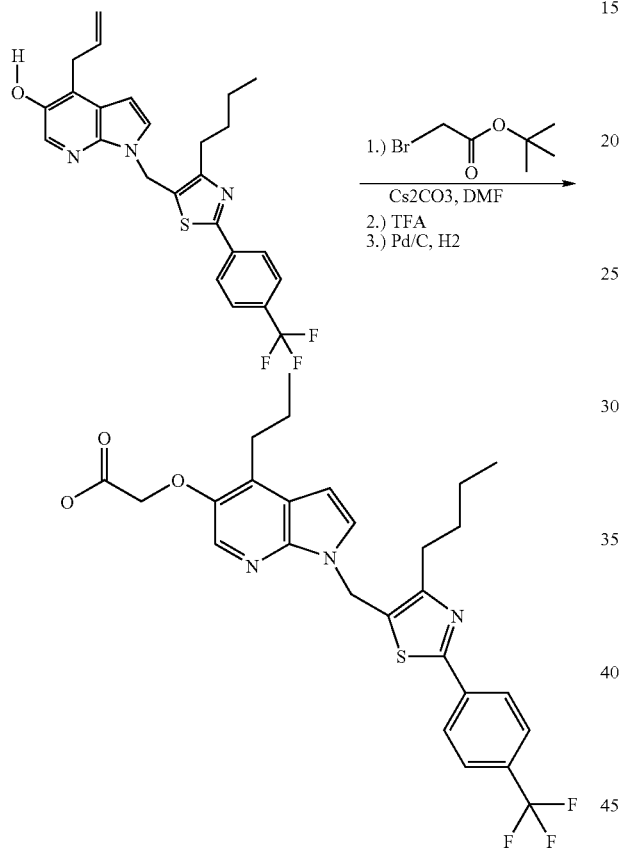

140 mg 4-Allyl-1-[4-butyl-2-(4-trifluoromethyl-phenyl)-thiazol-5-ylmethyl]-1H-pyrrolo[2,3- b]pyridin-5-ol were dissolved in 10 ml dimethylformamide and 195 mg cesium carbonate and 116 mg tert.-butylbromoacetate were added. The reaction mixture was stirred at room temperature for two hours when 100 ml ethyl acetate were added and the mixture was washed five times with portions of 20 ml of water The organic layer was dried over MgSO4 and the solvent removed under reduced pressure. The residue was dissolved in 10 ml dichloromethane and 4 ml trifluoroacetic acid were added. The reaction mixture was stirred at room temperature for three hours then 100 ml toluene were added and the solvents removed under reduced pressure. The residue was dissolved in 20 ml methanol and 50 mg palladium (10% on charcoal) were added. The reaction mixture was stirred at room temperature in a hydrogen atmosphere (5 bar) for one hour. The catalyst was filtered off and the solvent removed under reduced pressure. The residue was purified by RP-HPLC to provide 70 mg {1-[4-Butyl-2-(4-trifluoromethyl-phenyl)-thiazol-5-ylmethyl]-4-propyl-1H-pyrrolo[2,3-b]pyridin-5-yloxy}-acetic acid as colorless lyophilisate.

C27H28F3N3O3S (531.60), LCMS(ESI): 532.3 (M+H$^+$).

What is claimed is:
1. A compound of formula I:

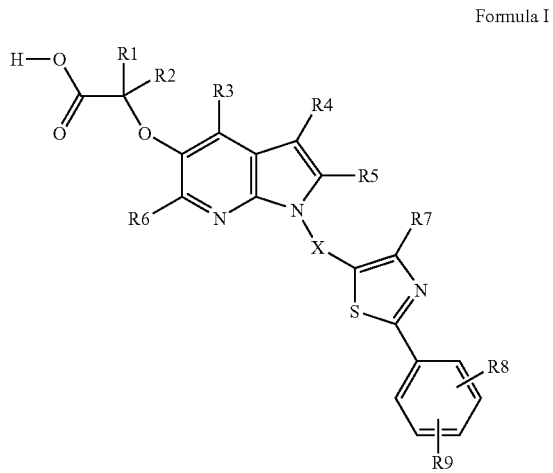

Formula I wherein

R1 and R2 are selected from the group consisting of H and (C1-C6)-alkyl, or R1 and R2 taken together with the carbon atom to which they are attached form a, (C3-C6)-cycloalkyl;

R3 is selected from the group consisting of H, F, Cl, Br, NO2, CN, CF3, SCH3, (C1-C6)-alkyl, (C2-C6)-alkenyl, and (C1-C4)-alkylene-O—(C1-C4)-alkyl R4 is H or (C1-C6)-alkyl, R5 is selected from the group consisting of H, (C1-C6)-alkyl, and (C1-C6) alkylene-phenyl, R6 is selected from the group consisting of H, F, Cl, Br, CN, CF3, SCH3, (C1-C6)-alkyl, and (C1-C4)-alkylene-O—(C1-C4)-alkyl;

R7 is selected from the group consisting of (C1-C6)alkyl, (C1-C4)alkylene-O—(C1-C4)alkyl, (C1-C6)alkylene-phenyl, (C1-C4)alkylene-O—(C1-C4)alkylene-phenyl, (C3-C6)cycloalkyl, (C2-C6)alkenyl, phenyl, O-phenyl, (C1-C6)alkylene-S(O)$_n$—(C1-C6)alkyl, (C1-C6)alkylene-NR10R11, (C1-C6)alkylene-CONR10R11, (C1-C6)alkylene-SO2NR10R11, (C1-C6)alkylene-NR10SO2-(C1-C6)alkyl, (C1-C6)alkylene-OCONR10R11, (C1-C6)alkylene-NR10COR11, and (C1-C6)alkylene-NR10CONR11, wherein alkyl may be optionally substituted with one or more fluorine or phenyl atoms and where n may be 0, 1 or 2;

R8 and R9 are independently selected from the group consisting of H, F, Cl, Br, CF$_3$, OCF$_3$, (C$_1$-C$_6$)-alkyl, O—(C$_1$-C$_6$)-alkyl, SCF$_3$, SF$_5$, OCHF$_2$, OCH$_2$F, OCF$_2$-CHF$_2$, O-phenyl, OH, and NO$_2$;

R10 and R11 are independently selected from the group consisting of H,(C1-C6)alkyl and (C3-C6)-cycloalkyl wherein the alkyl and cycloalkyl are optionally substituted with one to three F or heteroaryl; or R10 and R11 may together with the N atom to which they are attached form a 4, 5 or 6-membered saturated, partly saturated or unsaturated heterocycle ring wherein a carbon (C) atom may be replaced by N, O, S, SO or SO$_2$; and X is —CH2- or —CH2CH2-;
or a pharmaceutically acceptable salt thereof.

2. The compound of formula I as recited in claim 1 wherein R8 is hydrogen.

3. The compound of formula I as recited in claim 2, wherein R9 is in para-position.

4. The compound of formula I as recited in claim wherein:
R1 and R2 are H;
R3 is H or (C1-C6)-alkyl;
R4 is H;
R5 is H;
R6 is H;
R7 is independently selected from the group consisting of (C1-C6)alkyl, (C1-C4)alkylene-O—(C1-C4)alkyl, (C1-C6)alkylene-phenyl, (C1-C4)alkylene-O—(C1-C4)alkylene-phenyl, (C3-C6)cycloalkyl, (C2-C6)alkenyl, phenyl, O-phenyl ,(C1-C6)alkylene-S(O)$_n$—(C1-C6)alkyl, (C1-C6)alkylene-NR10R11, (C1-C6)alkylene-CONR10R11, (C1-C6)alkylene-SO2NR10R11, (C1-C6)alkylene-NR10SO2-(C1-C6)alkyl, (C1-C6)alkylene-OCONR10R11, (C1-C6)alkylene-NR10COR11 and (C1-C6)-alkylene-NR10CONR11 wherein alkyl may be optionally substituted with one or more fluorine atoms or phenyl and where n may be 0, 1 or 2;
R8 is H;
R9 is CF$_3$;
R10 and R11 are independently selected from the group consisting of H, (C1-C6)-alkyl and (C3-C6)-cycloalkyl wherein the alkyl and cycloalkyl are optionally substituted with one to three F or, heteroaryl; or R10 and R11 may together with the N atom to which they are attached form a 4, 5 or 6-membered heterocycle and wherein a C atom may be optionally replaced by N, O, S, SO, SO$_2$; and
X is —CH2-.

5. The compound of formula I as recited in claim 4 wherein;
R1 and R2 are both H;
R3 is H or (C1-C6)-alkyl;
R4 is H;
R5 is H;
R6 is H;
R7 is selected from the group consisting of (C1-C6)alkyl, (C1-C4)alkylene-O—(C1-C4)alkyl, (C1-C6)alkylene-phenyl, (C1-C4)alkylene-O—(C1-C4)alkylene-phenyl, (C3-C6)cycloalkyl, (C2-C6)alkenyl, phenyl, and O-phenyl, where alkyl may substituted with one or more fluorine or phenyl atoms and where n may be 0, 1 or 2;
R8 is H;
R9 is CF$_3$; and
X is —CH2-.

6. The compound of formula I as recited in claim 5 wherein:
R1, R2, R5 and R6 are H;
R3 is H or (C1-C6)-alkyl;
R4 is H;
R7 is (C1-C6)-alkyl;
R8 is CF3;
R9 is H; and
X is —CH$_2$-.

7. A pharmaceutical composition comprising one or more compounds of formula I as recited in claim 1 and a pharmaceutically acceptable carrier.

8. A pharmaceutical composition comprising one or more compounds of formula I as recited in claim 1 and one or more additional pharmaceutical active compounds which are therapeutically effective in the treatment of metabolic disturbances or disorders and a pharmaceutically acceptable carrier.

9. The pharmaceutical composition of claim 8 wherein said additional pharmaceutical active compound is selected from the group consisting of one or more anti-diabetic compounds.

10. The pharmaceutical composition of claim 8 wherein said additional pharmaceutical active compound is selected from the group consisting of one or more lipid modulators.

11. The pharmaceutical composition of claim 8 wherein said additional pharmaceutical active compound is selected from the group consisting of one or more anti-atherosclerotic agents.

12. The pharmaceutical composition of claim 8 wherein said additional pharmaceutical active compound is selected from the group consisting of one or more anti-obesity agents.

13. The pharmaceutical composition of claim 8 wherein said additional pharmaceutical active compound is selected from the group consisting of one or more anti-inflammatory agents.

14. The pharmaceutical composition of claim 8 wherein said additional pharmaceutical active compound is selected from the group consisting of one or more anti-thrombotic agents.

15. The pharmaceutical composition of claim 8 wherein said additional pharmaceutical active compound is selected from the group consisting of one or more pharmacological actives for the treatment of high blood pressure.

16. The pharmaceutical composition of claim 8 wherein said additional pharmaceutical active compound is selected from the group consisting of one or more pharmaceutical actives for the treatment of complications caused by diabetes.

17. A process for preparing a pharmaceutical comprising one or more of the compounds as claimed in claim 1 which comprises mixing the active compound with a pharmaceutically suitable carrier and bringing this mixture into a form suitable for administration.

\* \* \* \* \*